(12) United States Patent
Wilen

(10) Patent No.: US 8,186,381 B2
(45) Date of Patent: May 29, 2012

(54) SELECTION VALVE

(75) Inventor: Anders Wilen, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 503 days.

(21) Appl. No.: 12/523,358

(22) PCT Filed: Feb. 11, 2008

(86) PCT No.: PCT/SE2008/000110
§ 371 (c)(1),
(2), (4) Date: Jul. 16, 2009

(87) PCT Pub. No.: WO2008/103097
PCT Pub. Date: Aug. 28, 2008

(65) Prior Publication Data
US 2010/0032603 A1 Feb. 11, 2010

(30) Foreign Application Priority Data
Feb. 22, 2007 (SE) ...................................... 0700463

(51) Int. Cl.
F16K 11/06 (2006.01)

(52) U.S. Cl. ................. 137/625.11; 137/580; 73/61.55

(58) Field of Classification Search .................. 137/580, 137/625.11, 625.15, 625.46; 73/61.55
See application file for complete search history.

(56) References Cited

U.S. PATENT DOCUMENTS

| | | | | |
|---|---|---|---|---|
| 2,719,426 A * | 10/1955 | Lamb et al. | ........................ | 73/52 |
| 3,192,954 A * | 7/1965 | Gerhold et al. | .......... | 137/625.11 |
| 3,477,207 A | 11/1969 | Auger | | |
| 3,814,129 A * | 6/1974 | Cioffi | ........................ | 137/625.11 |
| 3,868,970 A | 3/1975 | Ayers et al. | | |
| 3,978,888 A * | 9/1976 | Naono | ........................ | 137/625.19 |
| 4,068,528 A * | 1/1978 | Gundelfinger | .............. | 73/864.84 |
| 4,158,630 A | 6/1979 | Stearns | | |
| 4,263,937 A * | 4/1981 | Rudenko | ........................ | 601/136 |
| 4,705,627 A | 11/1987 | Miwa et al. | | |
| 6,012,488 A * | 1/2000 | Nichols | ..................... | 137/625.11 |
| 6,155,123 A * | 12/2000 | Bakalyar | ..................... | 73/864.83 |
| 6,672,336 B2 * | 1/2004 | Nichols | ..................... | 137/625.46 |
| 6,904,936 B2 * | 6/2005 | Ma | .......................... | 137/625.47 |
| 7,503,203 B2 * | 3/2009 | Gamache et al. | ............ | 73/23.42 |
| 2003/0098076 A1 | 5/2003 | Nichols | | |

* cited by examiner

Primary Examiner — John Fox

(57) ABSTRACT

A rotary selection valve where different components can be selected in different rotation positions of the valve and furthermore the flow through the components can be reversed by rotating the rotary valve.

2 Claims, 6 Drawing Sheets

SELECTION VALVE

CROSS-REFERENCE TO RELATED APPLICATIONS

This application is a filing under 35 U.S.C. §371 and claims priority to international patent application number PCT/SE2008/000110 filed Feb. 11, 2008, published on Aug. 28, 2008, as WO 2008/103097, which claims priority to patent application number 0700463-3 filed in Sweden on Feb. 22, 2007.

FIELD OF THE INVENTION

The present invention relates to valves and more specifically to rotary valves for selecting a desired set of inlet/outlet ports out of a plurality of such sets.

BACKGROUND OF THE INVENTION

Valves are commonly used in devices that involve the transportation of a fluid. A typical type of valve, for example used in laboratory systems of moderate sizes such as a liquid chromatography system (LCS), is the rotary valve.

Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotator with respect to the stator.

Rotary valves can be designed to withstand high pressures (such as pressures above 30 MPa). They can be made from a range of materials, such as stainless steel, high performance polymeric materials and ceramics.

The number of inlets/outlets as well as the design of grooves in the rotator or the stator reflects the intended use of a specific valve.

A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

Another type of valve is used to select one of a set of components, each component having an inlet and an outlet. An example of this is the 6-port ST valve available from Valco Instruments Co. Inc., which is illustrated in FIG. 1.

Four components 121-124, herein illustrated as capillary loops, may be connected to the stator of the valve. The valve stator also has an inlet port 132 and an outlet port 131. The valve rotor has two grooves 125, 126. The outer groove 125, that is in fluid communication with the inlet port 132, has an inwardly radially extending portion that connects to one end 127 of the selected component 124. At the same time, the inner groove 126, that is in fluid communication with the outlet port 131, has an outwardly radially extending portion that connects to the other end 128 of the selected component 124.

Thus, the user may pass a flow through the selected component while the other components are isolated from the valve inlet/outlet. Provided that the flow direction through the valve is always the same, the flow direction through each component is determined by how it is connected to the valve.

However, sometimes the user wishes to alternate the flow direction through the component. For example, in the case that the component is a chromatography column it is sometimes desirable to load the column in one direction and then eluate the trapped content using a reversed flow direction. With a prior art valve similar to the one described above, it is then necessary to redirect the flow using additional means, such as a flow redirecting valve.

SUMMARY OF THE INVENTION

An object of the invention is to provide an improved component selection valve that is more convenient to use.

This object is achieved in a valve according to claim 1 of the present application. Hereby one single valve is provided having both the component selecting feature and the flow reversing feature.

DETAILED DESCRIPTION OF THE INVENTION

Figure 1:
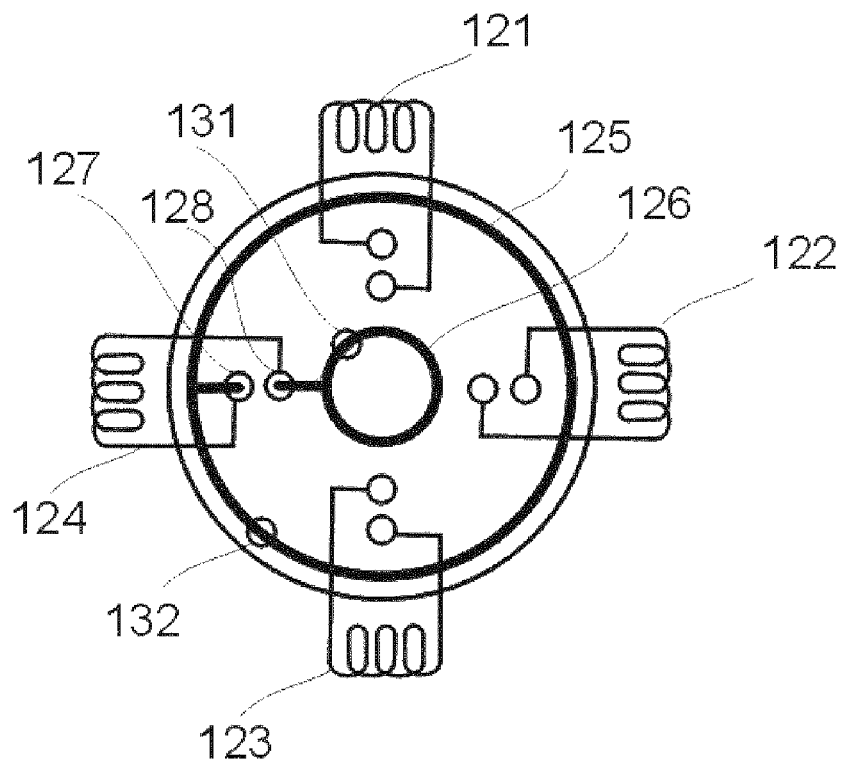
FIG. 1 is a schematic view of a prior art selection valve.
Figure 2:
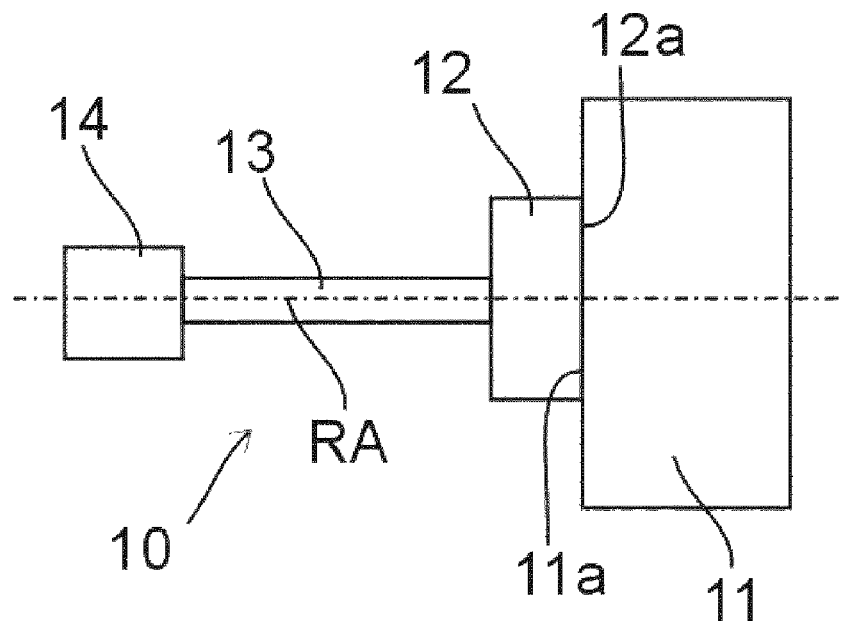
FIG. 2 is a schematic side view of a rotary valve.

The main parts of a typical rotary valve are schematically shown in FIG. 2 (wherein no brackets or similar load carrying or fastening elements are shown). The rotary valve 10 has a stator 11, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 11, which is fixed with respect to the instrument into which it is built, is provided with ports (not shown in FIG. 2) for fluid communication with a fluid source and any components with which the valve is to co-operate. The ports may be situated on any suitable position on the exterior surface of the stator. The ports are provided with means to connect capillaries or tubing. Such means may be of any suitable type, such as conventional Valco fittings well known to anyone skilled in the art. The ports are via channels in fluid communication with a corresponding set of orifices on an inner stator face 11a, i.e. that surface of the stator 11 that during operation is in contact with the rotor 12.

The rotor 12 is typically formed as a disc and has an inner rotor face 12a that is that face that is pressed against the inner stator face 11a during operation. The inner rotor face 12a is provided with one or more grooves which interconnect different orifices of the inner stator face 11a depending on the rotary position of the rotor 12 with respect to the stator 11.

Figure 3:
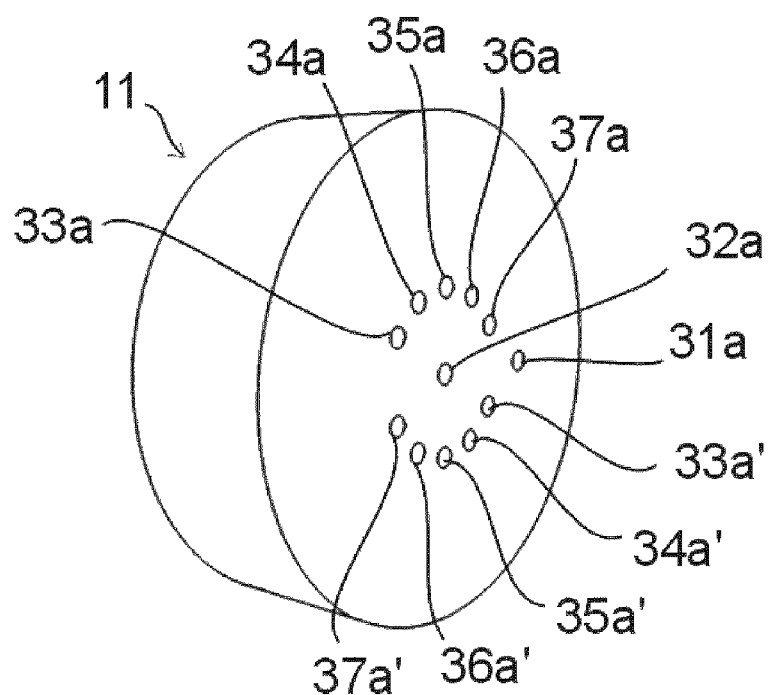
FIG. 3 shows the front side of a valve stator according to one embodiment of the invention.

FIG. 3, which shows a simplified perspective view of the front side of a stator 11, illustrates the inlet and outlet port 31a, 32a, 33a-37a, 33a'-37a' arrangement for a 12-port valve embodiment according to the present invention useful for selecting among up to five connected components. The front side is here the side of the stator 11 opposite the inner stator face 11a.

Generally, it should be noticed that the number of ports, the angular position of ports, grooves and similar shown in the figures of the present application could differ between different embodiments of the invention, i.e. they could be turned with respect to the rotary axis of the valve, mirrored or altered in other ways as long as their mutual co-operation is still according to the inventive idea.

In addition, since the inlet/outlet ports in the stator are connected to orifices on the inner stator face 11a via bores (or any type of channels) it is possible to arrange the ports in a way that differs from the pattern of orifices on the inner stator face 11a by making non-linear channels between the ports and the orifices. The ports into the stator can even be positioned on another outer surface of the stator than the front side. However, for reasons of simplicity, the ports are shown as being positioned in-line with the inner stator face orifices as will be described below in relation to FIG. 4.

Thus, the stator 11 of the embodiment according to FIG. 3 has ten ports that are used to connect five components to the valve. In FIG. 3, the reference numbers 33a and 33a' indicates the ports that in this example correspond to the connection of one such component. The other components will be connected to ports 34a, 34a', 35a, 35a', 36a, 36a' and 37a, 37a' respectively. Also shown in FIG. 3 is a central inlet port 32a and an outlet port 31a to and from, respectively, the valve.

As is understood by FIG. 3, a component is in this embodiment connected to diametrically opposed ports of the valve. It shall also be understood that the valve is similarly useful if the valve inlet and outlet are switched, i.e. if port 31a is used as inlet and port 32a as outlet, as will be clear from the description of the valve arrangement below.

The inlet port 32a receives a fluid flow from a main fluid source, such as a pump. From the outlet port 31a the fluid, is allowed to exit to the remaining part of the instrument or to any receptacle of choice.

The components attached to the valve may, in the case of use in a LCS, be chromatography columns or retaining loops, such as a conventional capillary loop. Since the valve according to the invention allows the flow to be reversed, any of the connection ports may be used as inlet as long as the other corresponding port acts as outlet or inlet, respectively.

Figure 4:
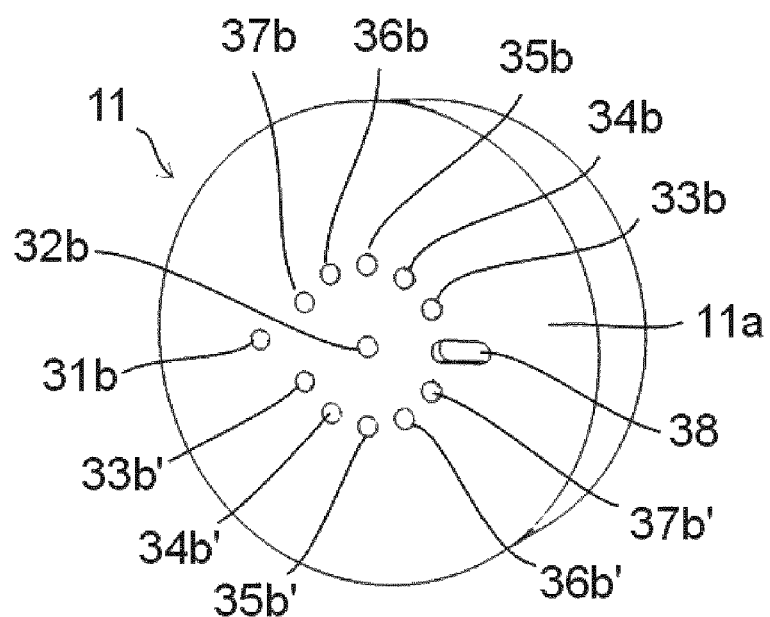
FIG. 4 shows the inner stator face of the stator of FIG. 3.

FIG. 4 is a perspective view of the stator 11 of FIG. 3 viewed from the other side, i.e. the inner stator face side 11a. Note that each port 31a, 32a, 33a, 33a'-37a, 37a' of the outer side of the stator is connected to the inner stator face 11a via a channel ending in an orifice 31b, 32b, 33b, 33b'-37b, 37b' shown in FIG. 4. A first component is associated with the ports/orifices 33a, 33a'/33b, 33b', a second component to the ports/orifices 34a, 34a'/34b, 34b' and so on.

In addition to the orifices 33-37b, 33-37b' which are in fluid connection with the ports, a groove 38 is in this embodiment provided in the inner stator face 11a. The groove is typically of essentially the same width as an orifice diameter. The valve according to the invention can be provided without this groove 38 but it is suitable to include the groove. The benefit of this groove 38 is described in detail below.

Figure 5:
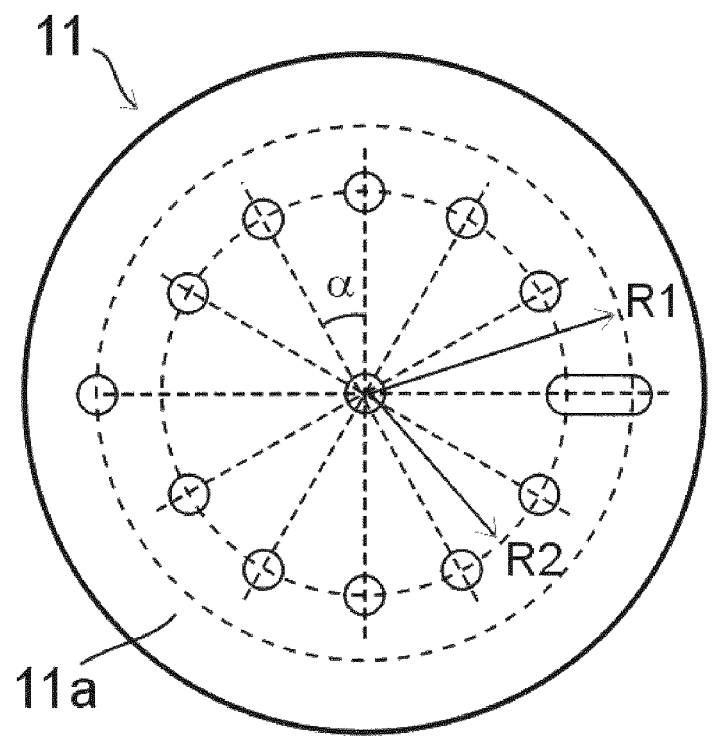
FIG. 5 shows the angular distribution of the orifices in the inner stator face according to one embodiment of the invention.

Looking at the inner stator face 11a, the general angular distribution of the orifices and the groove ends is illustrated in FIG. 5. The positions for orifices, groove ends and possibly also not used positions are in this embodiment substantially equally distributed around the central orifice of the stator (which center coincides with the rotary axis of the valve). Since there are twelve such positions on the stator according to this illustrated embodiment, the partition angle α is in this embodiment 30°. In other embodiments designed to allow for more or fewer connectable components, the angle may differ from 30°. Thus, in an embodiment for four connectable devices an angle α' of 36° is useful.

The outlet orifice (orifice 31b in FIG. 4) and the outer end of the groove 38 are in this embodiment placed on a radial distance R1 from the centre of the inner stator face 11a, while the orifices 33b, 33b'-37b, 37b' associated with the component ports 33a, 33a'-37a, 37a' and the inner end of the groove 38 are placed nearer the centre of the inner stator face 11a at a radial distance of R2.

As an example, in an embodiment having orifices with 0.5 mm diameter and a groove width of 0.5 mm, R1 is suitably 3 mm and R2 is suitably 2 mm.

Figure 6:
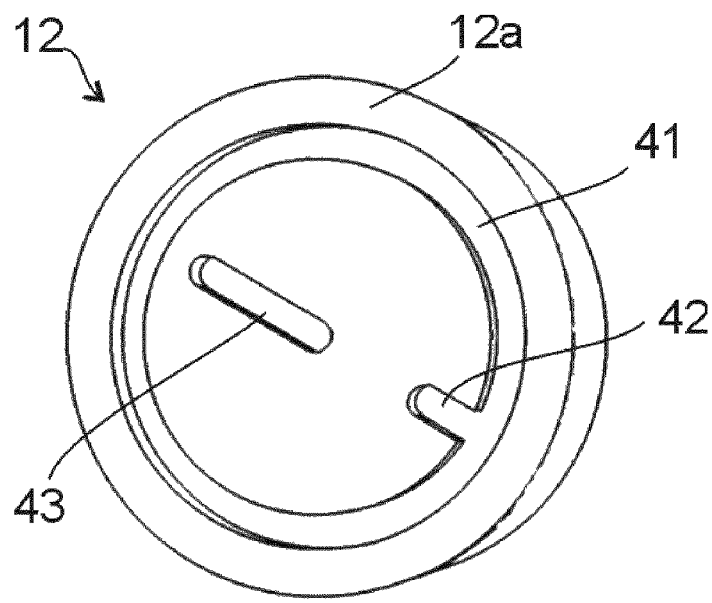
FIG. 6 shows the inner rotor face of a rotor according to one embodiment of the invention.

An inner rotor face 12a of a rotor 12 of a valve embodiment according to the present invention is shown in FIG. 6. This inner rotor face 12a is adapted to fit with the previously described embodiment of an inner stator face 11a illustrated in FIGS. 4 and 5. The inner rotor face 12a is provided with an essentially annular groove 41 and a radial groove 43. The annular groove 41 has in this embodiment an essentially annular shape with a radially inwardly extending extension 42. The radial groove 43 extends radially from the rotary centre of the inner rotor face 12a outwardly.

Figure 7:
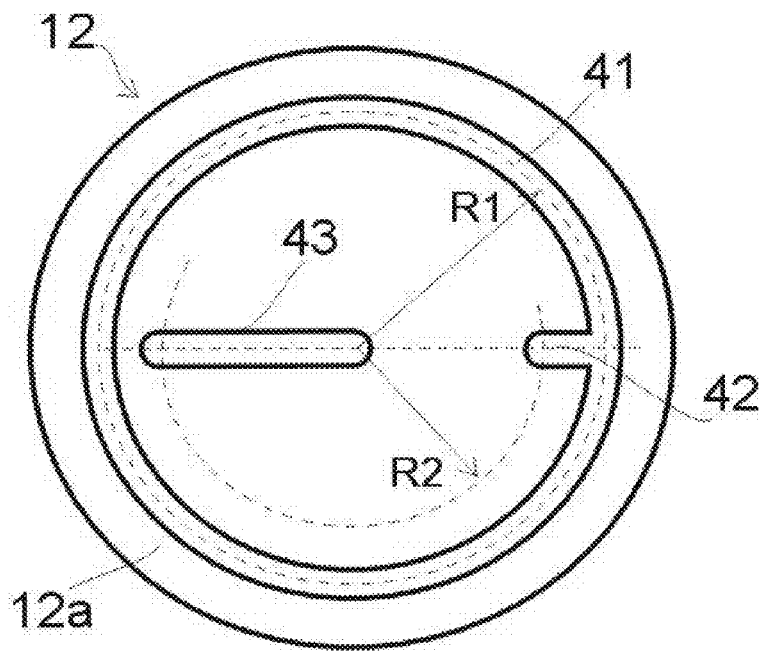
FIG. 7 shows the location of the grooves in the rotor of FIG. 6.

The geometry of the grooves 41, 43 is more clearly illustrated in FIG. 7. The annular groove 41 is placed at a radius R1, while its extension 42 extends to a radius R2 from the rotary centre of the inner rotor face. The radial groove 43 extends generally in line with the extension 42, but in opposite direction, from the rotary centre of the rotor face to a radial distance R2 from the centre. The distances R1 and R2 are the same as are used for the inner stator face 11a of FIG. 5. The width of the grooves 41-42 and 43 are typically the same as the orifice diameters.

The depths of the grooves of the stator as well as of the rotor may be selected to suit the dimensional flow rate of the valve, but is typically of the same order as the orifice diameter.

Figure 9:
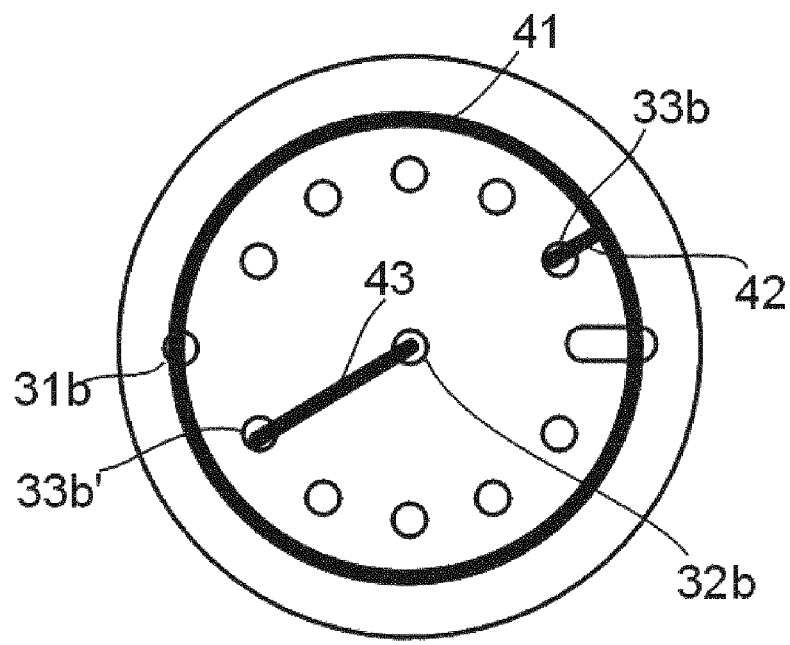
FIG. 9 is a schematic view of a second rotor position.
Figure 10:
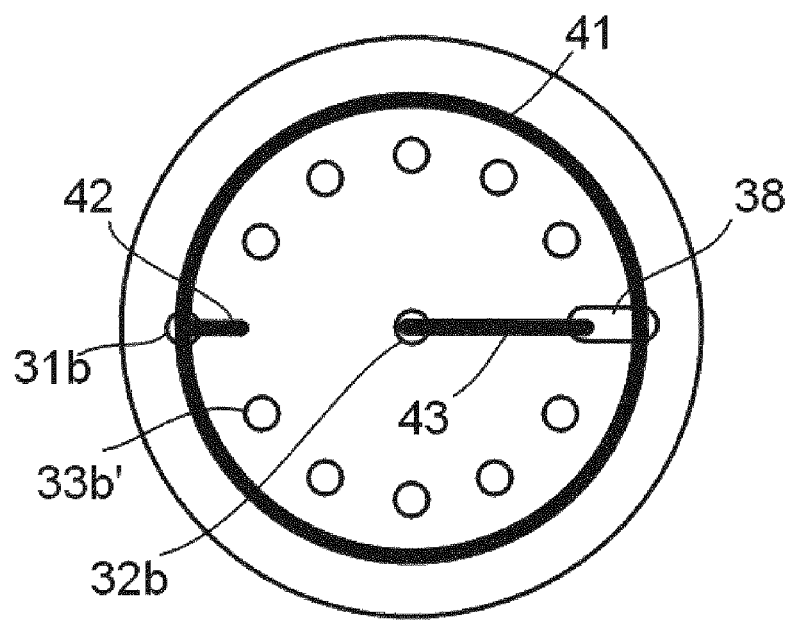
FIG. 10 is a schematic view of a third rotor position.

When assembled, the inner rotor face 12a is pressed against the inner stator face 11a in a manner that is typical for any conventional rotary valve (which is well known for anyone skilled in the art, and will not be explained herein). Depending on the mutual angular positions of the rotor 12 and the stator 11 different operation modes are obtained for the valve. These are illustrated in FIG. 8-10, wherein the grooves of the rotor are indicated by thick lines.

Figure 8:
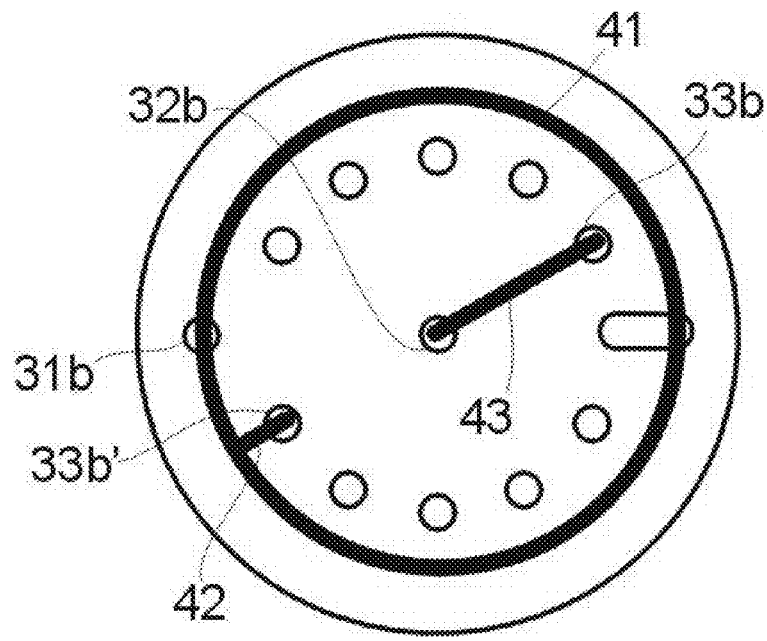
FIG. 8 is a schematic view of a first rotor position.

In a first rotor position, as shown in FIG. 8, the component orifice 33b (and thus the component port 33a) is connected with the valve inlet orifice 32b (and thus the valve inlet port 32a) via the radial groove 43. At the same time the annular groove 41 and its extension 42 connects the component orifice 33b' (and thus the component port 33a') with the valve outlet orifice 31b (and thus the valve outlet port 31a).

Provided that a component (not shown), such as a chromatography column or a capillary loop, is connected to the respective ports 33a and 33a', a fluid flow entering the valve via the inlet port 32a (and the inlet orifice 32b) will pass the radial groove 43, enter the component via orifice 33b and port 33a, pass the component and return back into the valve via port 33a' and orifice 33b', pass the extension 42 and the annular groove 41 to finally exit the valve via the outlet orifice and port 31b and 31a.

By rotating the rotor counterclockwise (when viewing FIG. 8) another pair of connection ports (such as 34a and 34a' in FIG. 4) will be connected to the valve inlet port 32a and outlet port 31a, thereby selecting another connected component.

FIG. 9 shows a second rotor position, wherein the rotor is rotated 180° with respect to the position shown in FIG. 8. In this position the same component is connected, but the flow direction is reversed. Thus, the fluid, still entering the valve via the inlet port 32a and the inlet orifice 32b, will pass the radial groove 43, enter the component via orifice and port 33b' and 33a', pass the component (in the reversed direction) and return back into the valve via port and orifice 33a, 33b, pass the extension 42 and the annular groove 41 to finally exit the valve via the outlet orifice and port 31b and 31a.

Thus, by simply rotating the rotor 180° the flow direction through the component is reversed without the need for any additional valves or any re-plumbing.

Furthermore, the illustrated embodiment allows for a third position, as shown in FIG. 10, wherein a connection between the valve inlet and outlet is provided, thereby enabling the flow to pass through the valve without entering anyone of the connected components.

In the bypass position, the fluid enters the central inlet port and orifice 32a and 32b, passes the radial groove 43 and the stator groove 38. Then it passes the annular groove 41 to exit the valve via the outlet orifice and port 31b and 31a. This position also allows the annular groove 41 to be rinsed.

Although the stator groove 38 is preferred in order to reduce the number of external ports, it is not essential for the invention. An external bypass could instead be provided by a further set of inlet/outlet ports (e.g. similar to the ports 33a and 33a') that are externally interconnected with a length of tubing. This could of course be made on any diametrical position of the valve, so that any of the inlet/outlet ports could be used as bypass ports.

The embodiment described above is only an example embodiment. It should be understood that the number of ports and orifices can be varied, thereby allowing for any other number of connected components. Furthermore the positions of the orifices and grooves can be slightly varied. The limiting feature is that the annular groove 41 should always be in fluid communication with the outlet orifice 31b, and not contact any of the other orifices, the radial groove 43 should always be in fluid contact with the inlet orifice 32b and be able to upon rotation reach all the connection orifices 33b-37b, 33b'-37b' and the extension 42 need to be able to upon rotation reach all the connection orifices. In order to obtain all advantages with the present invention, the components to be connected are connected to two diametrically opposite orifices and the extension 42 and the radial groove 43 are also diametrically opposite.

Figure 11:
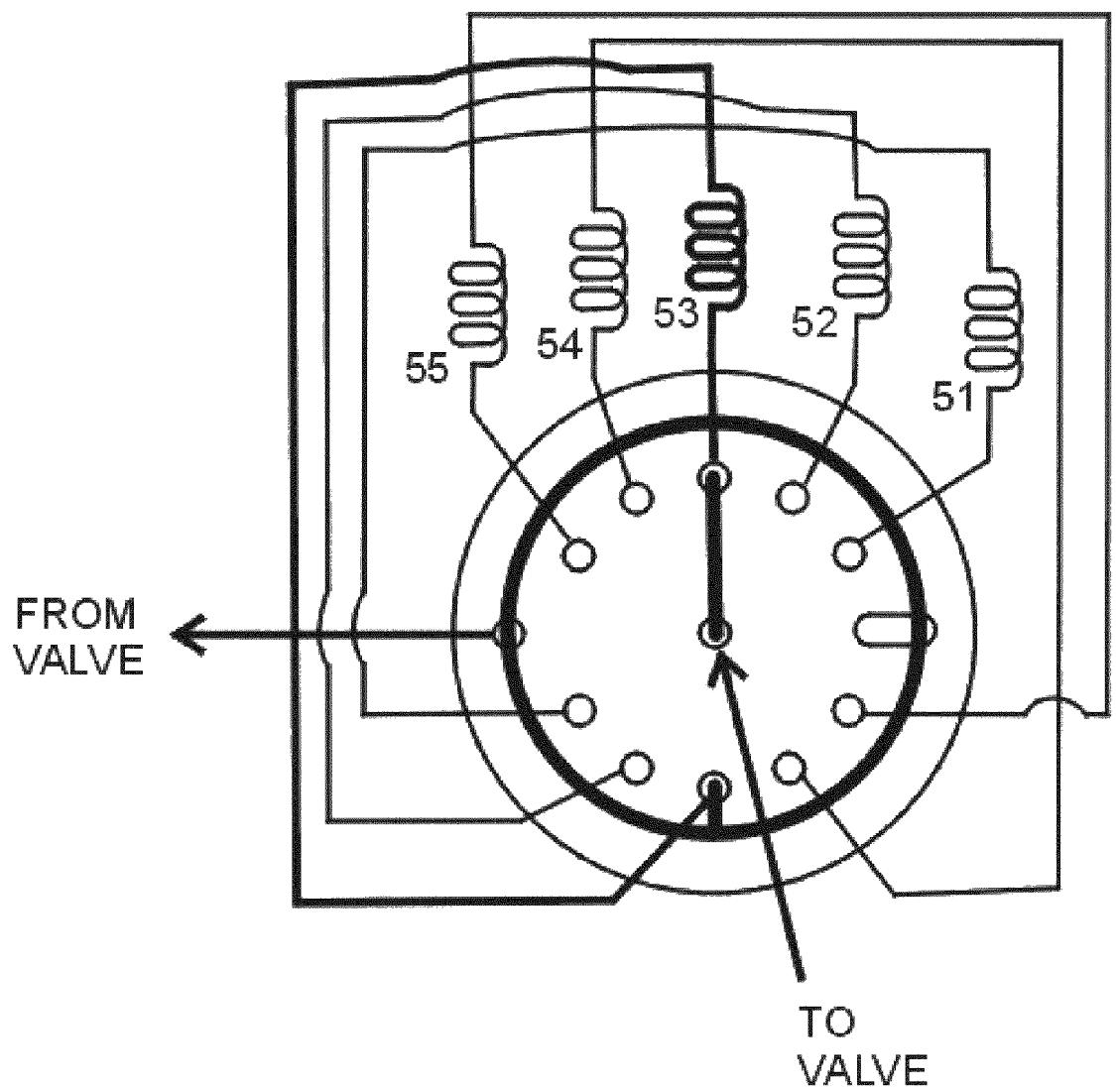
FIG. 11 is a schematic view of five components connected to a valve according to one embodiment of the invention.

FIG. 11 illustrates how five components 51-55 (in this case shown as capillary loops) are connected to the described valve embodiment. In this case, the valve rotor is shown in a position wherein the third component 53 is selected.

As described above the exact position of the orifices need not to be according to the embodiment described above. What is important for the invention is that the different grooves reaches the specific orifices that should be reached in each rotation position described above.

What is claimed is:

1. A rotary selection valve (10), the valve comprising a stator (11) and a rotor (12), said stator (11) comprising a number of connection ports protruding into the stator and each ending in an orifice on an inner stator face (11a), which is a face of the stator making contact in a fluid tight manner with an inner rotor face (12a) of the rotor (12), said inner rotor face (12a) being rotatably movable around a rotational axis (RA) relative to the inner stator face (11a), a number of different components are connected to the ports to the stator and they are selected in different rotation positions of the rotor, the inner stator face comprising:
   a first inlet/outlet orifice (31b) connected to a corresponding first inlet/outlet port (31a), said first inlet/outlet orifice (31b) being positioned at a first radial distance (R1) from the rotational axis of the rotor,
   a second inlet/outlet orifice (32b) connected to a corresponding second inlet/outlet port (32a), said second inlet/outlet orifice being positioned generally coinciding with the rotational axis of the rotor (12),
wherein the inner stator face further comprises:
   pair wise connection orifices (33b-37b, 33b'-37b'), each orifice communicating with a corresponding connection port (33a-37a, 33a'-37a') and the components to be connected to the valve is adapted to be connected to two ports each, the two orifices associated with each connectable component being placed at essentially diametrically opposite positions with respect to the rotational axis of the rotor and each said connection orifice (33b-37b, 33b'-37b') being positioned at a radial distance from the rotational axis of the rotor that is shorter than said first radial distance (R1),
wherein the inner rotor face comprises:
   an essentially annular groove (41) positioned around the rotational axis of the rotor at said first radial distance (R1), said annular groove (41) further having an extension (42) that extends from one position of the annular groove (41) towards, but not the whole way to the rotational center of the rotor with a length such that it can reach all of the connection orifices (33b-37b, 33b'-37b'), and
   a radial groove (43) extending from the rotational center of the rotor and to a length such that it can reach all of the connection orifices (33b-37b, 33b'-37b') but shorter than the first radial distance (R1), said radial groove (43) being generally diametrically positioned with respect to the direction of the extension (42) of the annular groove (41).

2. The rotary selection valve of claim 1, wherein the inner stator face (11a) further comprises a stator groove (38) positioned diametrically opposite to the first inlet/outlet orifice 31b, said stator groove 38 extending radially between the first radial distance R1 and to essentially the same length as the radial groove (43) is extended to from the rotation center.

* * * * *